(12) United States Patent
Velez

(10) Patent No.: US 10,573,150 B2
(45) Date of Patent: Feb. 25, 2020

(54) FLOW ALARM

(71) Applicant: Michael D. Velez, Huntington Beach, CA (US)

(72) Inventor: Michael D. Velez, Huntington Beach, CA (US)

(73) Assignee: Michael D. Velez, Huntington Beach, CA (US)

( * ) Notice: Subject to any disclaimer, the term of this patent is extended or adjusted under 35 U.S.C. 154(b) by 0 days.

(21) Appl. No.: 16/352,656

(22) Filed: Mar. 13, 2019

(65) Prior Publication Data

US 2019/0213859 A1 Jul. 11, 2019

Related U.S. Application Data

(63) Continuation of application No. 15/679,051, filed on Aug. 16, 2017, now Pat. No. 10,269,225, which is a continuation of application No. 15/286,041, filed on Oct. 5, 2016, now Pat. No. 9,773,393.

(60) Provisional application No. 62/299,481, filed on Feb. 24, 2016, provisional application No. 62/238,273, filed on Oct. 7, 2015.

(51) Int. Cl.
| | |
|---|---|
| *G08B 21/02* | (2006.01) |
| *A61M 16/10* | (2006.01) |
| *A61M 16/06* | (2006.01) |
| *A61M 16/00* | (2006.01) |
| *G01F 15/18* | (2006.01) |

(52) U.S. Cl.
CPC ......... *G08B 21/02* (2013.01); *A61M 16/0051* (2013.01); *A61M 16/0616* (2014.02); *A61M 16/10* (2013.01); *A61M 2016/003* (2013.01); *A61M 2202/0208* (2013.01); *A61M 2205/14* (2013.01); *A61M 2205/15* (2013.01); *A61M 2205/183* (2013.01); *A61M 2205/186* (2013.01); *A61M 2205/44* (2013.01); *A61M 2205/581* (2013.01); *G01F 15/185* (2013.01)

(58) Field of Classification Search
CPC ... G08B 21/02; A61M 16/10; A61M 16/0616; A61M 2016/003; A61M 2205/15; A61M 2205/186; A61M 2205/183; A61M 2202/0208; G01F 15/185
See application file for complete search history.

(56) References Cited

U.S. PATENT DOCUMENTS

| | | | | |
|---|---|---|---|---|
| 3,297,255 A * | 1/1967 | Fortman | ............... | B05B 1/265 116/137 A |
| 3,595,228 A * | 7/1971 | Simon | ............... | A61M 16/0051 128/202.22 |
| 4,067,329 A * | 1/1978 | Winicki | ............ | A61M 16/0051 128/202.22 |
| 4,316,182 A * | 2/1982 | Hodgson | ............... | A61B 5/0816 128/202.22 |
| 4,669,415 A * | 6/1987 | Boord | ................... | A62B 9/006 116/70 |
| 5,626,129 A * | 5/1997 | Klimm | ............. | A61M 16/0051 128/202.22 |

(Continued)

*Primary Examiner* — Ryan W Sherwin
(74) *Attorney, Agent, or Firm* — K&L Gates LLP; Louis C. Cullman; Brian J. Novak

(57) ABSTRACT

Described are gas flow disruption alarms. The alarms can include a gas inlet; a gas outlet configured to couple to a gas delivery device; and a vibration member between the gas inlet and the gas outlet configured to produce an audible sound when a gas delivery device is removed from the gas outlet.

20 Claims, 8 Drawing Sheets

(56) References Cited

U.S. PATENT DOCUMENTS

| | | | | |
|---|---|---|---|---|
| 5,836,302 | A * | 11/1998 | Homuth | A61M 16/0051 128/205.23 |
| 6,386,196 | B1 * | 5/2002 | Culton | A61M 16/0051 128/205.23 |
| 6,679,432 | B1 * | 1/2004 | Arnold | A61F 7/0097 128/202.22 |
| 7,298,280 | B2 * | 11/2007 | Voege | G01P 13/0013 340/606 |
| 7,730,847 | B1 * | 6/2010 | Redd | A61M 16/08 116/112 |
| 7,896,401 | B2 * | 3/2011 | Richards | A61M 16/16 285/386 |
| 8,707,950 | B1 * | 4/2014 | Rubin | A61M 16/06 128/202.27 |
| 9,186,528 | B2 * | 11/2015 | Patil | A62B 17/006 |
| 2003/0189492 | A1 * | 10/2003 | Harvie | A61M 16/0051 340/573.1 |
| 2007/0017515 | A1 * | 1/2007 | Wallace | A61M 16/0051 128/204.23 |
| 2008/0053441 | A1 * | 3/2008 | Gottlib | A61M 16/0051 128/204.23 |
| 2010/0020529 | A1 * | 1/2010 | Brooks | A61M 16/08 362/34 |
| 2011/0248856 | A1 * | 10/2011 | Obenchain | A61M 16/20 340/606 |
| 2013/0068221 | A1 * | 3/2013 | Mian | A61M 16/0051 128/202.22 |
| 2015/0170630 | A1 * | 6/2015 | Dawson | G01M 3/26 116/112 |

* cited by examiner

FLOW ALARM

CROSS REFERENCE TO RELATED APPLICATIONS

This application is a continuation of U.S. patent application Ser. No. 15/679,051, filed Aug. 16, 2017, which is a continuation of U.S. patent application Ser. No. 15/286,041, filed Oct. 5, 2016, now U.S. Pat. No. 9,773,393, which claims the benefit of U.S. Provisional Patent Application No. 62/299,481, filed Feb. 24, 2016, and U.S. Provisional Patent Application No. 62/238,273, filed Oct. 7, 2015, the entire disclosures each of which are incorporated herein by reference.

FIELD

The present application describes devices that produce an audible alarm when a disconnection of gas flow apparatus occurs.

SUMMARY

Described herein are devices that can provide an alert when gas flow apparatus become at least partially disconnected. In some embodiments, the devices can provide an audible alarm.

In some embodiments, gas flow disruption alarms are described. The alarms can include: a gas inlet; a gas outlet configured to couple to a gas delivery device; and a vibration member between the gas inlet and the gas outlet. The vibration member can be configured to produce an audible sound when a gas delivery device is removed from the gas outlet.

In some embodiments, the gas inlet can be configured to attach to a gas source. The gas source can be a pressurized gas tank, an air pump, a rechargeable gas tank, a gas distribution system, or a combination thereof. The gas source can supply various gases that can be helium, nitrogen, argon, hydrogen, oxygen, carbon dioxide, halon, Freon, compressed air, propane, butane, carbon monoxide, hydrogen sulfide, ammonia, methane, nitrogen dioxide, acetylene, or propylene. In one embodiment, the gas is oxygen or another gas that can be hazardous or otherwise dangerous if leaked into a surrounding area.

In some embodiments, the vibration member is located within a body portion. The body portion can include an internal pipe that extends beyond the body portions' proximal end and is connected to the gas outlet. In other embodiments, the body portion can be sealed against the internal pipe thereby creating an internal volume between an interior surface of the body portion and an exterior surface of the internal pipe.

In some embodiments, the vibration member can be configured to attach and seal proximal end of the internal pipe thereby sealing the internal volume. In other embodiments, the vibration member can be configured to extend over the internal pipe thereby sealing the interior of the internal pipe from the internal volume. In still other embodiments, the vibration member can be configured to expand or lift at least partially off internal pipe thereby creating the audible sound when the gas delivery device is removed from the gas outlet.

In some embodiments, the audible sound created by the devices described herein when disconnection occurs can have various characteristics that make it distinct and/or unique. The audible sound can have a frequency of at most about 400 Hz. Further, in some embodiments, the audible sound can be characterized as a musical note. The musical note can be a D note. In other embodiments, the musical note can be a D above middle C. Still other embodiments the note can be described as sharp of a D. In still other embodiments, the sound can be characterized as a horn.

In some embodiments, devices described herein can be configured to produce the audible sound when a disconnection occurs and a low flow rate exists through a device. In some embodiments, the low flow rate is less than about 15 L/min. In other embodiments, the low flow rate can less than about 10 L/min or less than about 5 L/min.

Methods are also described herein for using the alarm devices. The methods can include attaching a gas flow disruption alarm between an oxygen gas source and a patient oxygen delivery line, wherein the gas flow disruption alarm is configured to produce an audible sound when the patient oxygen delivery line is disconnected from the gas flow disruption alarm. In some embodiments, the oxygen gas source is a hospital gas distribution system.

Kits are also described herein including an alarm device and instructions for use of the device. Some embodiments describe kits including a device, a patient breathing device and instructions for use.

DETAILED DESCRIPTION

Figure 1:
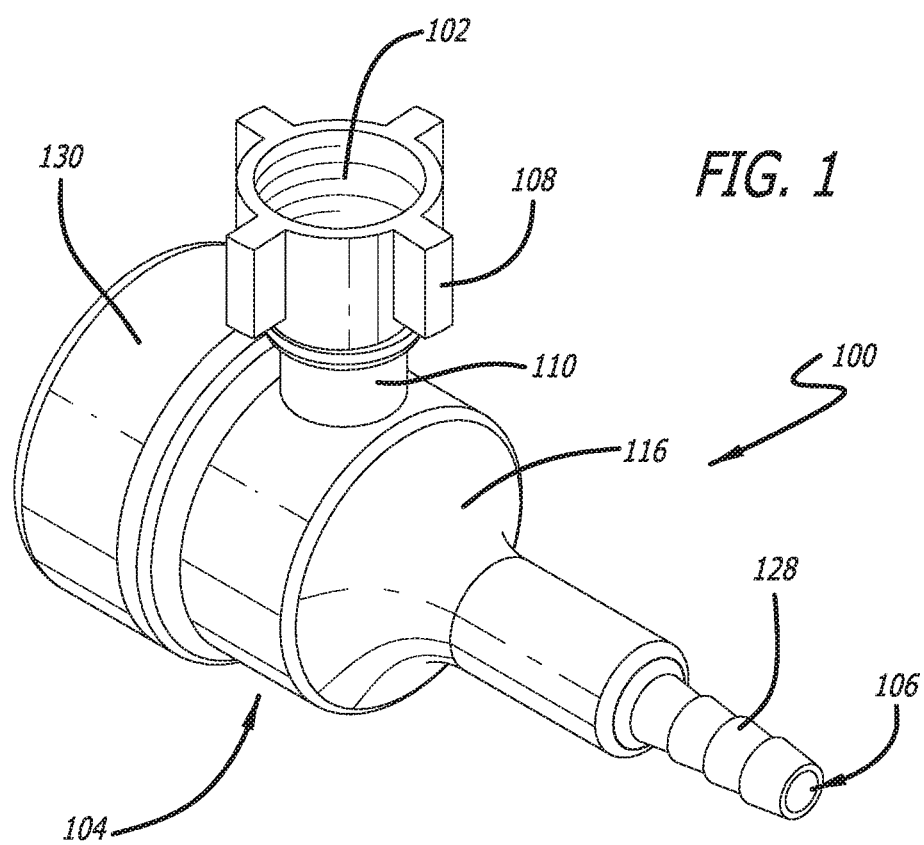
FIG. 1 is a perspective view of a non-limiting alarm device as described herein.
Figure 2:
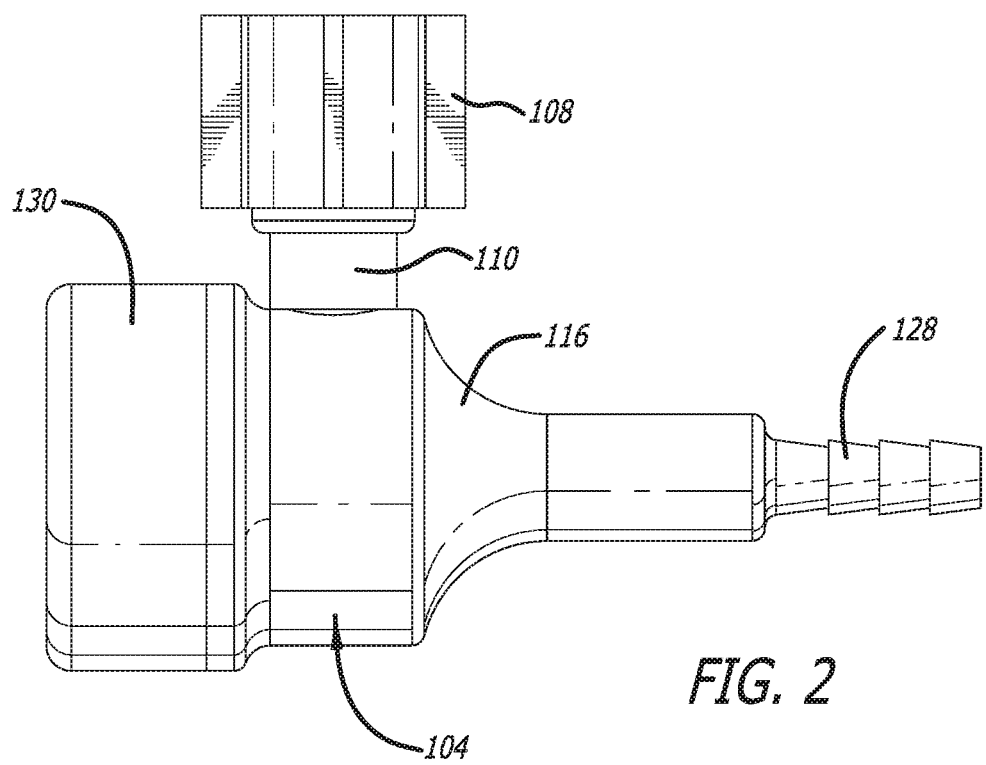
FIG. 2 is a side view of the non-limiting alarm device illustrated in FIG. 1.

Described herein generally are gas flow disruption alarm devices. The devices can provide an alarm such as an audible alarm when gas flow has been disrupted. Gas flow can be defined as any flow of gas through the herein described devices. Flow can be from an inlet to an outlet or from an outlet to an inlet. Flow disruption can be a partial or complete disconnection. Devices described herein can in some embodiments be referred to as disconnect or disconnector horns.

The presently described alarm devices can function in many industries in which a gas needs to be dispensed from one place to another. In the medical industry, the gas is often oxygen and patients need or are dependent on increased concentrations of oxygen. Examples of gas delivery devices to patients are nasal cannulas, facemasks, venti-masks, and bag valve masks.

Problems exist with oxygen delivery devices in that they tend to disconnect because the interface between the gas outlet and connected hose is not standardized. This leads to a situation in which a patient's flow of oxygen is interrupted. To compound the problem, there is no reliable way to identify this common occurrence, as low-pressure gas distribution systems do not have alarms. Whoever is caring for the patient needs to notice the oxygen is running but the end of the oxygen delivery device is no longer connected. These disconnections are difficult to identify.

Oxygen dependent patients are often delirious, demented or being actively sedated and cannot tell you they are feeling the effects of hypoxia. This can lead to a catastrophic event such as hypoxic brain injury or death if not identified in time. To compound the problem, unidentified disconnections from a gas source lead to continuous expulsion of gas into the ambient environment. Open oxygen flowmeters are often found running many hours or even days after a patient has been discharged. This is an expensive waste of resources. Also, many gases have noxious or deleterious effects to the surrounding environment. Further, an open oxygen source can be a major fire risk in a patient care setting. The herein described flow disruption alarm devices alleviate and/or remedy some or all of these problems.

A non-limiting alarm device 100 is illustrated in FIGS. 1-4. Alarm device 100 includes a gas inlet port 102, a body section or portion 104, and a gas outlet port 106.

Gas inlet port 102 can be configured to interface with a gas source. Gas sources can be sources of gas that can provide a flow of the particular gas through gas inlet port 102. Gas sources can include, but are not limited to stand-alone pressurized gas tanks, air pumps, rechargeable gas tanks, gas distribution systems, auxiliary common gas outlets (ACGO), auxiliary oxygen flowmeters such as those on anesthesia machines, and the like, or combinations thereof.

Gases delivered to gas inlet port 102 can be virtually any gas. Non-limiting gases that can be delivered to gas inlet port 102 can be helium, nitrogen, argon, hydrogen, oxygen, carbon dioxide, halon, Freon, compressed air, propane, butane, carbon monoxide, hydrogen sulfide, ammonia, methane, nitrogen dioxide, acetylene, propylene, and the like. In some embodiments, the gas is a harmful or hazardous gas if the gas escapes or is not well controlled and/or contained.

Gas inlet port 102 can include a connection mechanism 108 that allows alarm device 100 to connect to a gas source. Connection mechanism 108 can be any mechanism that securely connects alarm device 100 to a gas source. Connection mechanism 108 can be, but is not limited to, a female or male threaded connection, barbed connection, force fit connection, or the like.

Gas inlet port 102 can be connected to body portion 104 through connection tube 110. However, in some embodiments, connection tub 110 is not needed and inlet port 102 feeds directly into body portion 104.

In one embodiment, gas inlet port 102 is a female internal threaded coupling that can couple onto a hospital gas delivery tap from a gas distribution system. In embodiments, a hospital gas distribution system can deliver oxygen. In some embodiments, the threading can be designed to the specifications of the Diameter Index Safety System (DISS) as standardized by the Compressed Gas Association. The compressed gas association created DISS so that one cannot connect threaded connections of different gases together, so as to prevent connecting a wrong gas and/or undesired gas. In one embodiment, the thread described herein can be a DISS oxygen thread. In one embodiment, an oxygen thread is called DISS 1240 with a 9/16"-18 threaded connection. Other DISS threads can be used herein to provide gas flow disruption alarms specifically for different types of gasses.

In other embodiments, the gas flow disruption alarms described herein can have a standard thread size and include various DISS thread adapters allowing a standard gas flow disruption alarm to be used with different gas sources fitted with DISS threads.

Body portion 104 can house an internal pipe 112 that extends beyond proximal end 114 of body portion 104. Body portion 104 can be sealed against pipe 112 that extends beyond the distal end 116 of body portion 104. This seal can create an internal volume 118 between interior surface 120 of body portion 104 and exterior surface 122 of pipe 112.

Proximal end 114 of body portion 104 can be fitted with a vibration member 124 that attaches and seals to perimeter 126 of proximal end 114 thereby sealing internal volume 118. Vibration member 124 can extend over internal pipe 112 at proximal end 123 of internal pipe 112 thereby sealing interior of the pipe from internal volume 118 until vibration member 124 is expanded or lifted at least partially off proximal end 123 of internal pipe 112 thereby creating an audible sound.

The audible sound can be any sound at any frequency that can be heard by a mammal. In some embodiments, a mammal can be a human. In other embodiments, the mammal can be a canine, feline, or the like. The sound can be at a frequency sufficient to provide an audible sound. The frequency can be between about 100 Hz and about 500 Hz, between about 200 Hz and about 400 Hz, between about 250 Hz and about 350 Hz, between about 275 Hz and about 300 Hz, between about 290 Hz and about 300 Hz, at least about 100 Hz, at least about 200 Hz, at least about 250 Hz, at least about 275 Hz, at least about 290 Hz, at most about 500 Hz, at most about 400 Hz, at most about 300 Hz, or about 298 Hz. In some embodiments, the frequency can be about 294 Hz.

In some embodiments, the audible sound can be a musical note. In other embodiments, the note can be a D. In various embodiments, the note can be a D above middle C or sharp of D. In some embodiments, the sound can be described as a horn sound.

Vibration member 124 can be made or formed of any material that can vibrate or resonate at a frequency that can create the audible sound. Materials suitable for vibration member 124 can be, but are not limited to, rubber, latex, polychloroprene, nylon, or a combination thereof.

Internal pipe 112 can extend beyond distal end 116 of body portion 104 and terminate at gas outlet port 106. Gas outlet port can be configured to interface with virtually any gas delivery device or device that requires gas flow or gas delivery.

Gas outlet port 106 can include a connection mechanism 128 that allows alarm device 100 to connect to a gas delivery device or device that requires gas flow or gas delivery. Connection mechanism 128 can be any mechanism that securely connects alarm device 100 to a gas delivery device or device that requires gas flow or gas delivery. Connection mechanism 128 can be, but is not limited to, a female or male threaded connection, barbed connection, force fit connection, or the like. In one embodiment, connection mechanism 128 is a barbed fitting.

Figure 5:
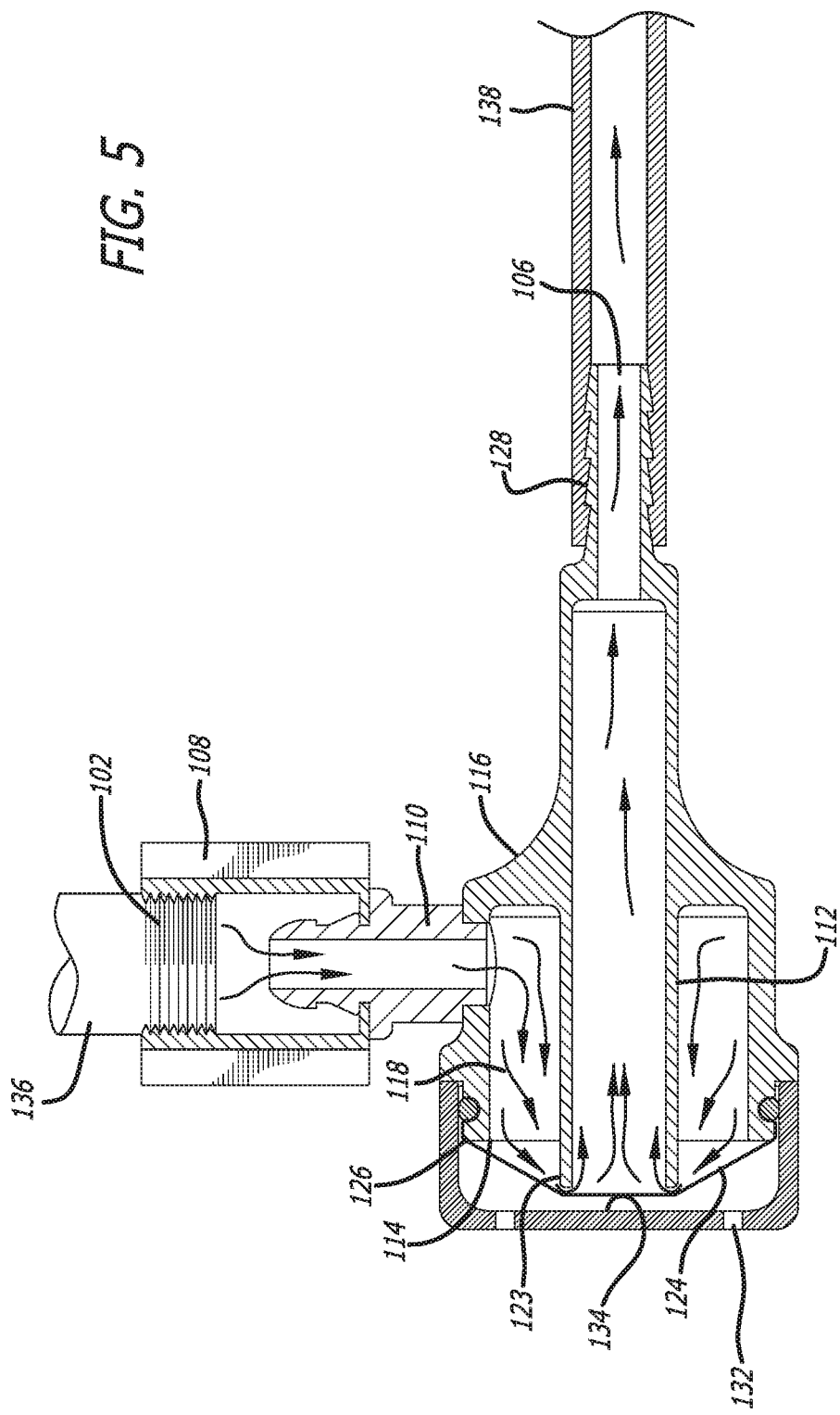
FIG. 5 is a side cross-sectional view of the non-limiting alarm device illustrated in FIG. 1 attached to a gas delivery device or device that requires gas flow or gas delivery as described herein.
Figure 6:
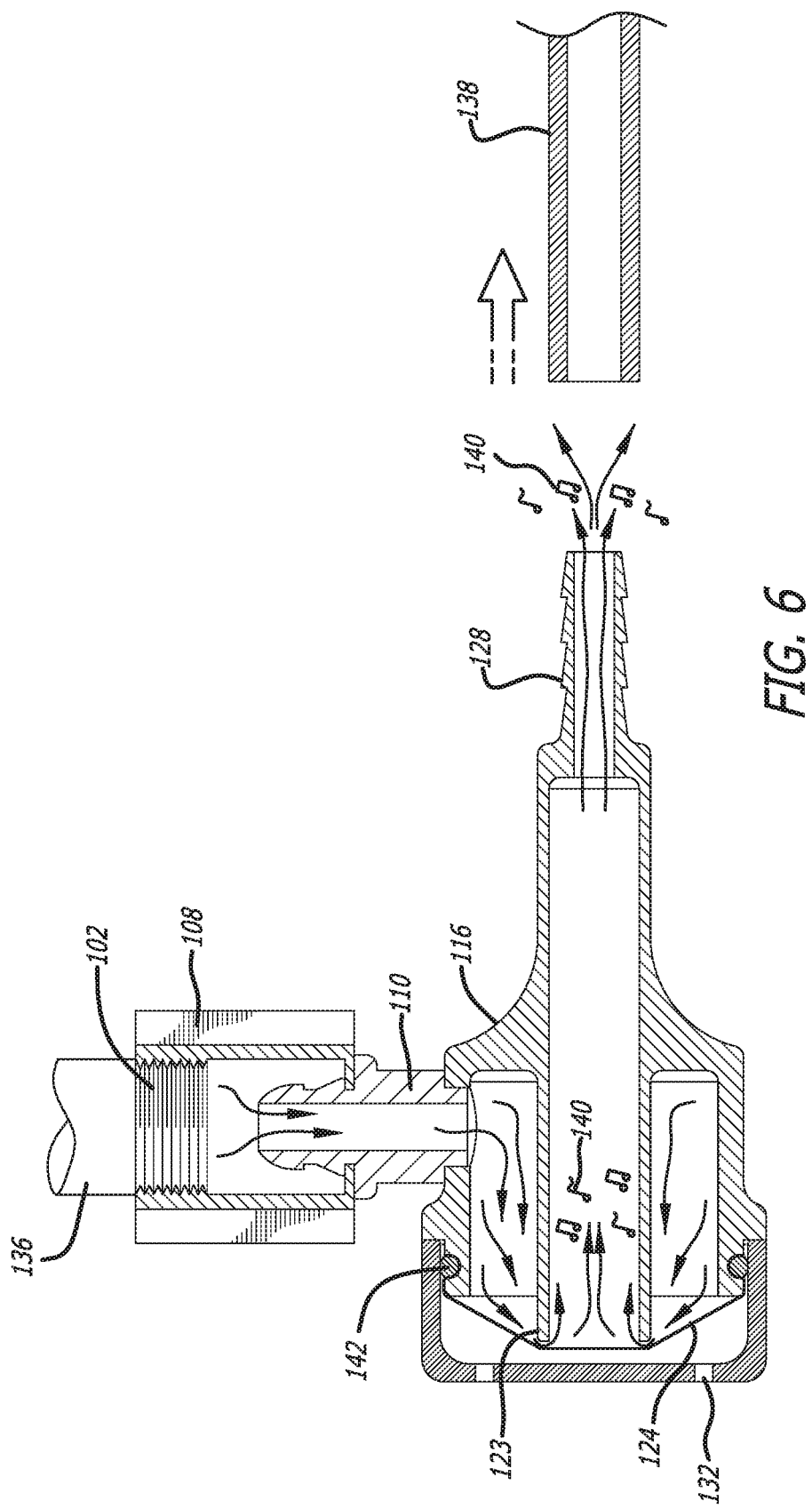
FIG. 6 is a side cross-sectional view of the non-limiting alarm device illustrated in FIG. 5 with the gas delivery device or device that requires gas flow or gas delivery disconnected and an audible sound emanating from the alarm device.

Non-limiting gas delivery devices or devices that require gas flow or gas delivery through gas outlet port 106 can be ventilation tubes such as nasal cannulas, ventilation masks such as face masks, bag valve masks, vacuums, vacuum lines, leak detection equipment, venturi masks, non-rebreather masks, and partial non-rebreather masks, respirators, therapeutic gas delivery devices, pneumatic tools and machinery, torches, burners, ovens, gas distribution systems, and the like. A non-limiting functional embodiment is illustrated in FIGS. 5-6. As illustrated in FIG. 5, alarm device 100 can be connected to a gas source 136 using connection mechanism 108. Gas flows from gas source 136 into gas inlet 102.

Alarm device 100 can be configured such that when connection mechanism 108 is connected to a gas source and a flow of gas is fed into gas inlet port 102, internal volume 118 fills with the gas and pushes vibration member 124 off of internal pipe 112 allowing the gas to exit through gas outlet port 106 and into a gas delivery device or device that requires gas flow or gas delivery. In FIG. 5, the gas delivery device or device that requires gas flow or gas delivery is a tube 138.

In some embodiments, gas inlet port 102 and gas outlet port 106 can be revered meaning that gas can flow into gas outlet port 106 and out of gas inlet port 102. In other words, in some embodiments, flow can be reversed and the alarm device can still function.

As illustrated in FIG. 6, alarm device 100 can further be configured such that when a gas delivery device or device that requires gas flow or gas delivery is disconnected, an audible sound 140 is produced. In one embodiment, when tube 138 is removed from gas outlet port 106 when gas is flowing through alarm device 100 from gas source 136, audible sound 140 can be produced.

In other embodiments, when tube 138 or another gas delivery device or device that requires gas flow or gas delivery is disconnected from gas outlet port 106, vibration member vibrates as gas passes from internal volume 118 into internal pipe 112 and creates audible sound 140 described herein. This audible sound alerts surrounding individuals that tube 138 or a gas delivery device or device that requires gas flow or gas delivery has been disconnected from gas outlet port 106 while gas is flowing through alarm device 100 from gas source 136.

This alert for disconnection from gas outlet port 106 can be beneficial because gas that may be flowing to a gas delivery device or device that requires gas flow or gas delivery through alarm device 100 can be hazardous. For example oxygen or hydrogen that is leaking into a room as a result of disconnection from gas outlet port 106 can be hazardous in that it can be a fire hazard. Other gases can be harmful if inhaled or can deprive individuals in the room of breathable air. Thus, alarm device 100 can alert of a disconnection to prevent harm from individuals in the surrounding area.

Further, an alert for disconnection from gas outlet port 106 can be beneficial to a person relying on gas delivery. In some embodiments, medical patients may rely on, for example, oxygen flowing through alarm device 100 and into breathing apparatus to sustain life. In some instances, these medical patients may not possess the ability to alert medical staff of a gas disconnection which can be a life-threatening event. Instances where this may be the case include patients that are unconscious, anesthetized, demented, delirious, nonverbal at baseline, or otherwise sedated for surgery or another medical procedure, emergency medical circumstances where a patient may not be alert or unconscious, or instances where a patient is conscious and too weak or feeble to respond. Thus, alarm device 100 can alert of a disconnection to prevent harm to patients that rely on the flowing gas to survive.

In some embodiments, as illustrated, alarm device 100 can include a cap 130. Cap 130 can be configured to cover vibration member 124 and protect it from physical damage. Cap 130 can attach to proximal end 114 of alarm device 100. Cap 130 can include a hole 132 that allows pressure between backing 134 of cap 130 and vibration member 124 to an atmospheric pressure or a pressure that does not differ substantially from atmospheric pressure. Alternatively or in addition to hole 132, portions of cap 130 can be a mesh protection network allowing air through while providing protection to vibration member 124.

Cap 130 can be attached to alarm device 100 in such a way that it provides protection to a vibration member. Attachments can include, but are not limited to friction fit, screw, adhesive coupling, melting, soldering, welding, and the like.

Further, cap 130 can be configured to secure vibration member 124 in place and seal it to perimeter 126 of proximal end 114 as described. This sealing can be by friction, adhesive, an o-ring 142, and the like, or a combination thereof. This sealing also prevents air from escaping between vibration member 124 and perimeter 126.

Figure 3:
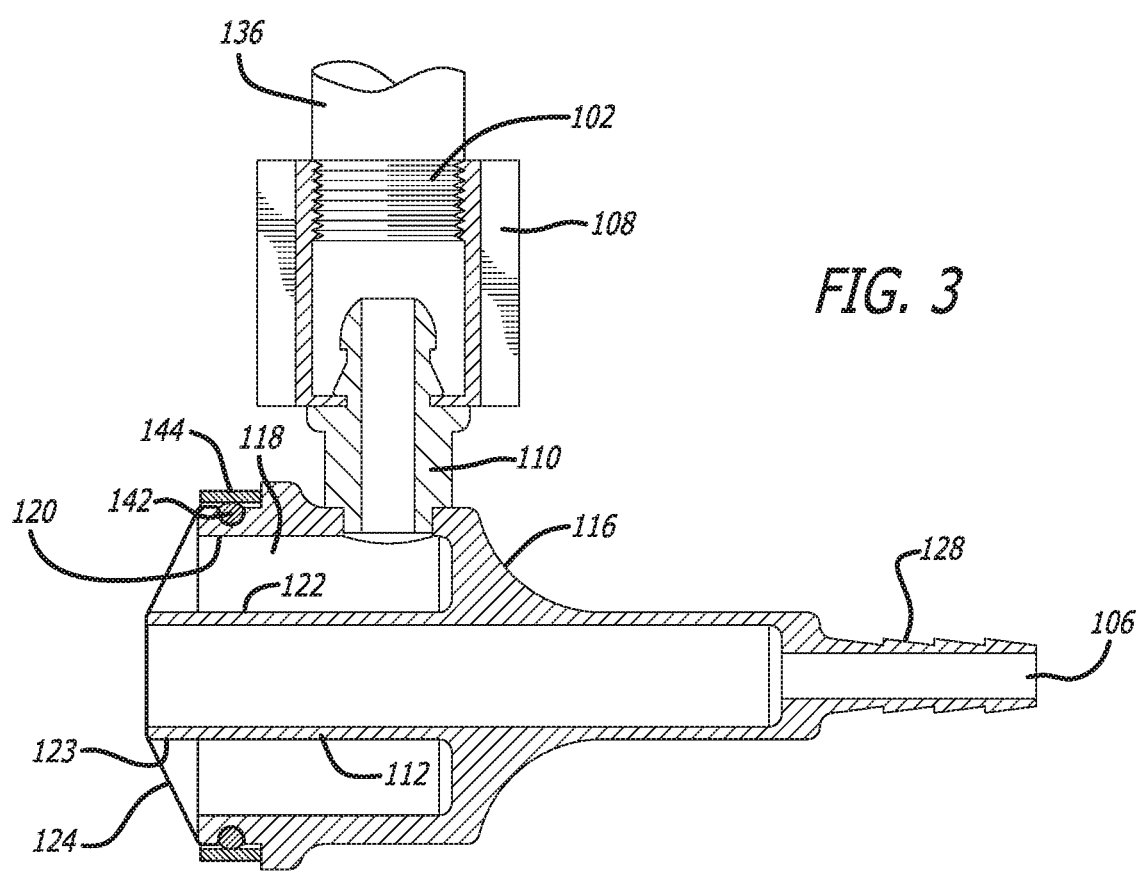
FIG. 3 is a side view of the non-limiting alarm device illustrated in FIG. 1 without a cap over the vibration member.
Figure 4:
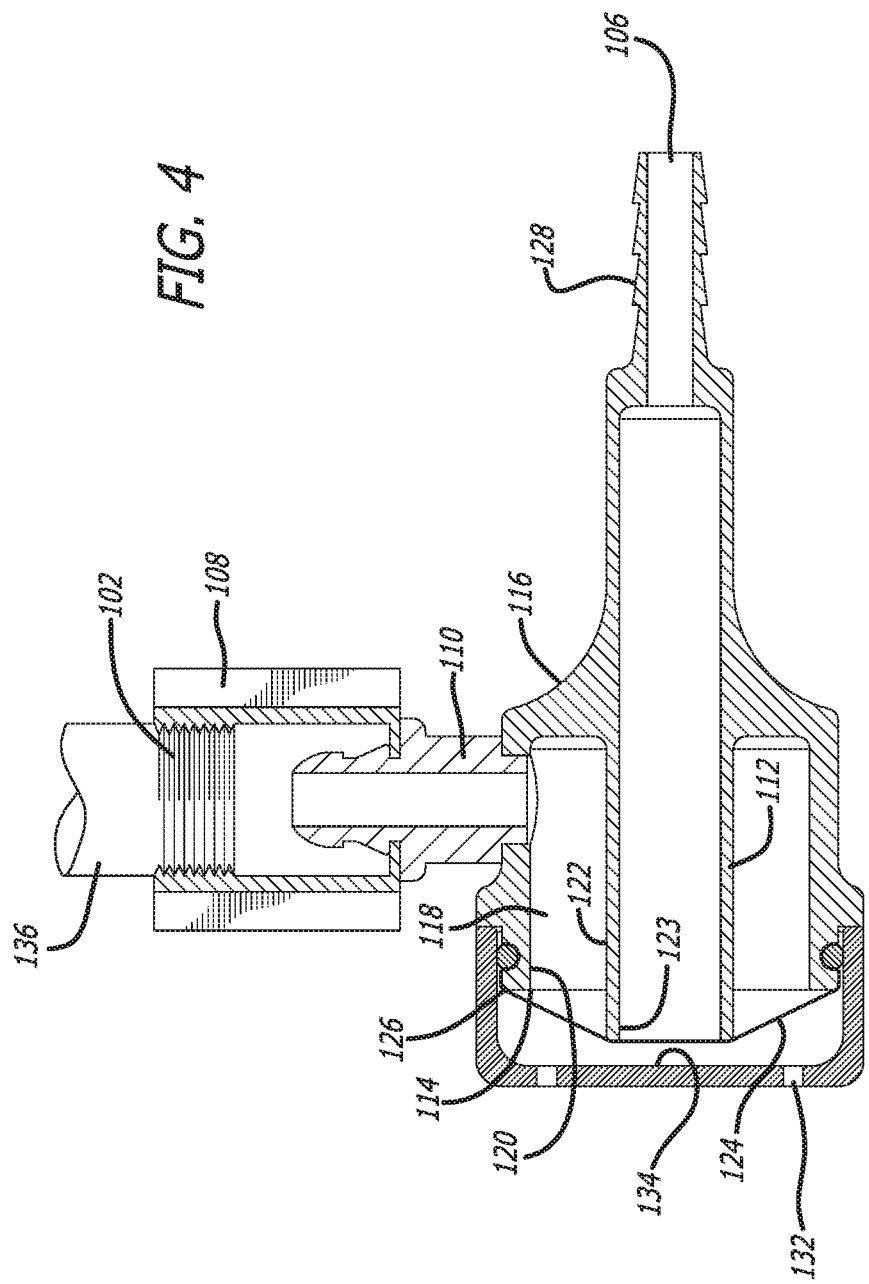
FIG. 4 is a side cross-sectional view of the non-limiting alarm device illustrated in FIG. 1.

In some embodiments as illustrated in FIG. 3, a cap may not be required. If a cap is not used, vibration member can be secured and/or sealed in place using an adhesive, o-ring 142, clamp 144 (such as a ring clamp), and the like, or a combination thereof. In some embodiments, only an adhesive may hold vibration member to perimeter 126.

In some embodiments, the devices described herein can be configured to provide an audible alarm sound when a low flow rate exists through a device. A low flow rate can be less than about 25 L/min, less than about 20 L/min, less than about 15 L/min, less than about 10 L/min, less than about 9 L/min, less than about 8 L/min, less than about 7 L/min, less than about 6 L/min, less than about 5 L/min, less than about 4 L/min, less than about 3 L/min, less than about 2 L/min, between about 2 L/min and about 10 L/min, between 2 L/min and about 5 L/min, or at least 1 L/min.

In some embodiments, a flow rate may need to be of a particular value in order for the alarms to function. In some embodiments, the flow is at least about 0.05 L/min, at least about 0.1 L/min, at least about 0.5 L/min, or at least about 1 L/min.

In some embodiments, the devices described herein may not function or are not configured to function at high flow rates. For example, devices that actuate whistles would not work in the present embodiments because the flow rate would be too low. Thus, the herein described devices may not be considered high flow devices.

In some embodiments, gas can be pushed through the alarm devices described herein. In other embodiments, gas can be pulled through the alarm devices described herein. In some embodiments, the alarm devices can function with some type of flow through the device.

The devices described herein can be formed of different parts that can be assembled during manufacturing or on site prior to use. The parts can be formed from processes such as injection molding, 3D printing, cast molding, pressing, or the like.

The parts can be formed of metals, polymers, or a combination thereof. The parts described herein are formed of polymers and/or metals that are rigid enough to hold a particular configuration and perform its intended function. In some embodiments, the polymer used is a thermal set rigid plastic.

In some embodiments, if used for medical purposes, alarm devices can be formed of any appropriate medical grade material.

Metals can include, but are not limited to, brass, steel, iron, aluminum, copper, zinc, alloys thereof, or combinations thereof. Polymers can include, but are not limited to polyurethanes, silicones, polyesters such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; carboxymethyl cellulose; synthetic and natural rubbers such as polysiloxanes, latex, polymerized isoprene, bromo isobutylene isoprene, chloro isobutylene isoprene, polychloroprene, chlorosulphonated polyethylene, ethylene propylene, ethylene propylene diene monomer, fluoro silicone, hydrogenated nitrile butadiene, polyisoprene, isobutylene isoprene butyl, methyl vinyl silicone, acrylonitrile butadiene, acrylonitrile butadiene carboxy monomer, styrene butadiene, epichlorodydrin; and combinations thereof.

Alarm devices can have various sized parts depending on a particular range of flow rates. In one embodiment, pipe 112 can have an internal diameter of about 0.7 cm, about 0.8 cm, about 0.9 cm, about 1 cm, about 1.1 cm, about 1.2 cm, about 1.3 cm, about 1.4 cm, about 1.5 cm, or between about 0.8 cm and about 1.2 cm. Further, pipe 112 can have an external diameter of about 1 cm, about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, or between about 1.1 cm and about 1.5 cm.

Further still, interior surface 120 of body portion 104 can be cylindrical and have an internal diameter of about 2 cm, about 2.1 cm, about 2.2 cm, about 2.3 cm, about 2.4 cm, about 2.5 cm, about 2.6 cm, about 2.7 cm, about 2.8 cm, about 2.9 cm, about 3 cm, between about 2.4 cm and about 2.8 cm.

Although measurements are given as diameters and imply a cylindrical configuration for the parts, other cross-sectional configurations can be used to provide an audible sound as described herein. For example, cross-sectional shapes can include, ellipses, ovals, squares, rectangles, pentagons, hexagons, heptagons, octagons, nonagons, 11 or more sided shapes, substantially circular shapes, parallelograms, trapezoids, or any other rectilinear shape.

The alarm devices described herein can be configured to be reusable or disposable. In one embodiment, the alarm devices can be reusable. In such a case, devices can be washable and sterilizable using conventional sterilization techniques. For example, the devices can be configured to allow multiple washings with a detergent or alcohol based cleaner without damaging the device. Further, for example, the devices can be sterilized using gamma irradiation, autoclave, or other sterilization techniques.

In other embodiments, the alarm devices can be configured to be disposable. Such single use devices are generally used for a single procedure or event and then discarded in an appropriate manner.

Methods are also described herein for using the alarm devices described herein. The methods can include attaching an alarm device between a gas source and a device that uses the gas or a tube delivering the gas. Then, a gas is turned on so that a flow of gas travels through alarm device and out to a device or into a tube. This attachment arms the alarm device because when the device or tube is disconnected from the alarms device when gas is flowing through, the alarm device produces an audible sound.

In some embodiments, the alarm devices described herein can aid an institution in saving money. Often, gas remains in the "on" position often overnight without needing to be simply because it was overlooked. This can be both dangerous, for example some gases can be hazardous and/or flammable and can be expensive as gas is being wasted. With the present alarm devices, if a gas is left on and tubing or a device is disconnected, the audible sound will alert surrounding individuals that the gas is still on. The gas can then be shut off thereby saving money and reducing a potential hazard.

If disconnected from an alarm device, a device or tube can be reconnected to the alarm device to stop the audible sound. Once reconnected, the alarm device is re-armed and can alert of any subsequent disconnections.

Figure 7:
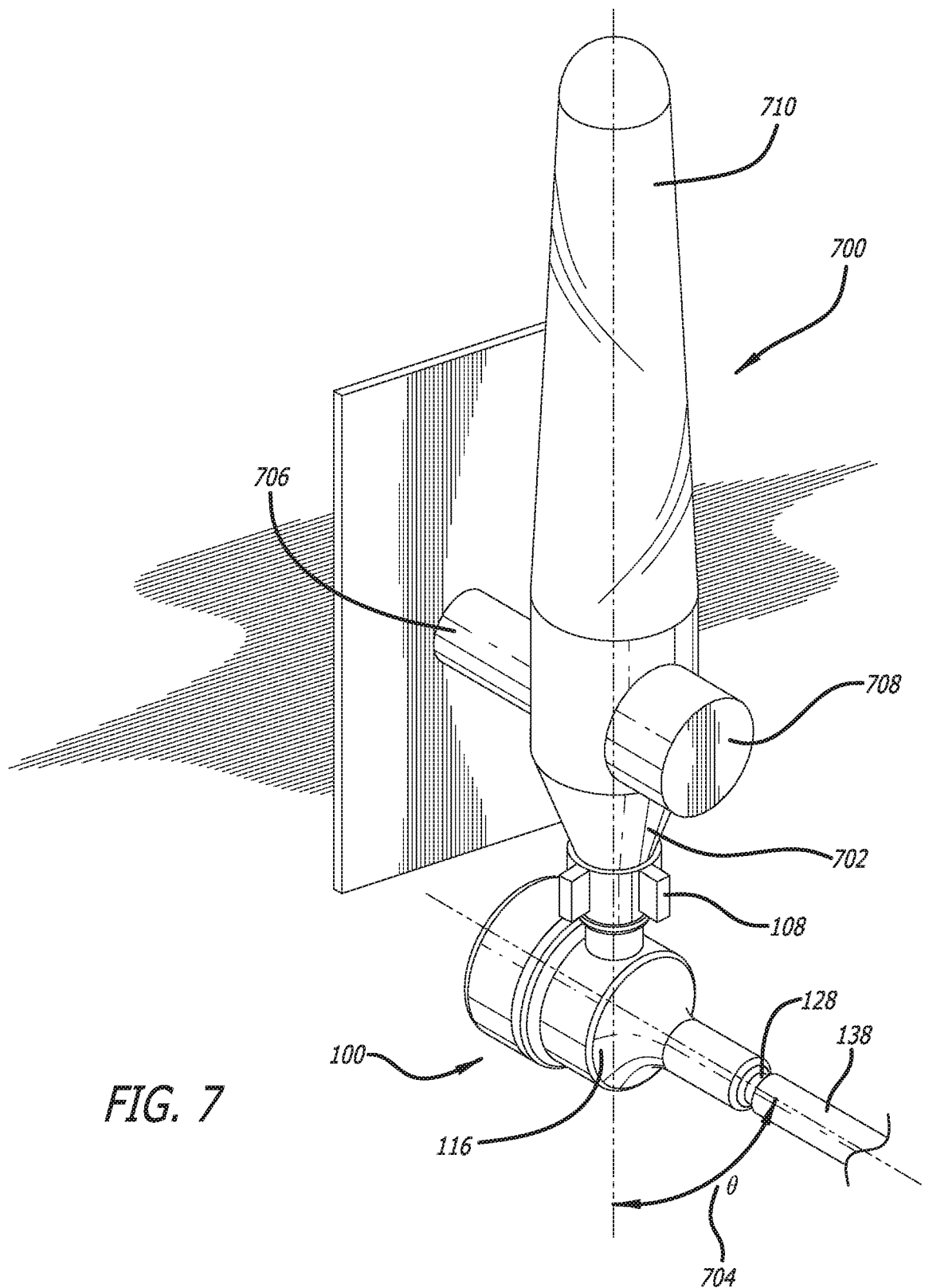
FIG. 7 is an illustration of the alarm device of FIG. 1 attached to a hospital oxygen delivery apparatus.

In one embodiment, as illustrated in FIG. 7, alarm device 100 can be attached to a medical gas delivery system 700. Such medical gas delivery systems can be located in hospital rooms, physician offices, operating rooms, ambulances, medical helicopters, medical airplanes, and the like. These systems, in some embodiments can be configured to deliver oxygen to a patient generally through a mask or nasal cannula that may be represented by or associated with tube 138.

Medical gas delivery system 700 generally has a tube or other device connected to interface area 702. In a conventional operation, a tube is connected vertically to a barb which in turn is threaded onto interface area 702. This configuration can lead to disconnections resulting from gravity and/or gravity can aid in a disconnection resulting from the tube being tugged off the barb. However, using alarm device 100, tube 138 can connect to connection mechanism 128 horizontally thereby reducing the assistance of gravity to a possible disconnect. Thus, in addition to alerting people around an alarm device of a possible disconnect, alarm device 100 can also assist in preventing accidental disconnects by reducing the downward forces on tube 138.

In some embodiments, connection mechanism 128 can be configured to be at an angle 704 less than 180 degrees relative to connection mechanism 108. Angle 704 can be less than about 180 degrees, less than about 120 degrees, less than about 100 degrees, less than about 90 degrees, less than about 75 degrees, less than about 45 degrees, about 90 degrees, about 45 degrees, about 120 degrees, or between about 120 degrees and about 45 degrees.

Medical gas delivery system 700 can generally be supplied with a gas such as oxygen through feed line 706. Gas flow can be adjusted using dial 708 and flow rate can be read on gauge 710. One common issue is that if a tube is disconnected from medical gas delivery system 700 while a gas such as oxygen is flowing into a tube, gauge 710 will not change to a substantial degree to alert anyone of the disconnection. The presently described alarm devices, such as alarm device 100, are configured to produce an audible sound when tube 138 is disconnected from connection mechanism 128. This audible sound can be used to alert physicians, EMTs, nurses, hospital employees, other medical personnel, surrounding individuals and the like that a disconnection has occurred and for the necessary person(s) to initiate a reconnection.

Figure 8:
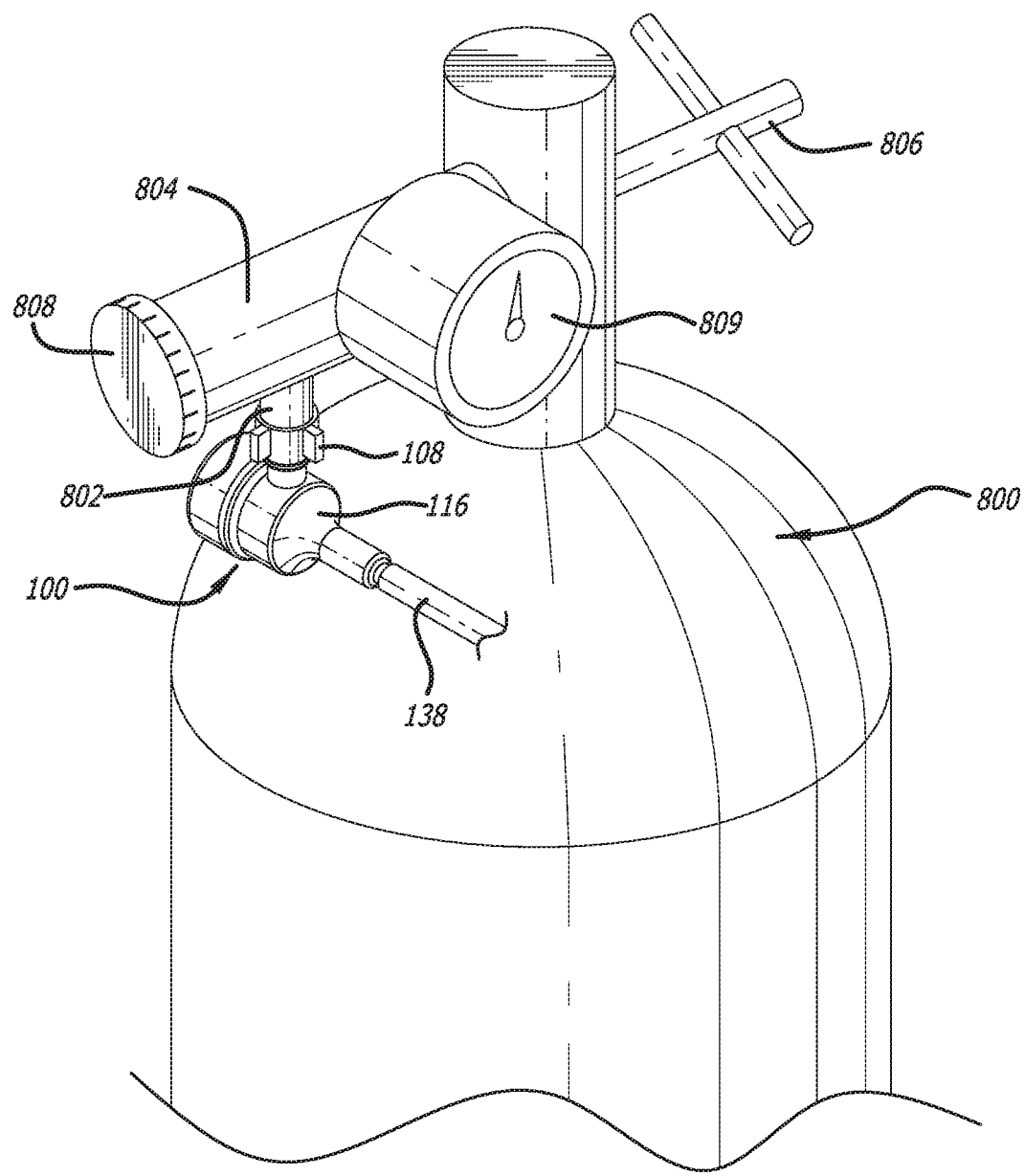
FIG. 8 is an illustration of the alarm device of FIG. 1 attached to a compressed gas tank.

In another embodiment, as illustrated in FIG. 8, alarm device 100 can be attached to a gas cylinder 800. Such gas cylinders systems can be located in ambulances, hospitals, physician offices, research labs, fire engines, manufacturing plants, machine shops, auto shops, or any other location where a compressed gas cylinder may be used. These systems can be configured to deliver a compressed gas through tube 138 to a delivery device at the other end of the tube.

Gas cylinder 800 generally has a tube or other device connected to interface area 802. Gas cylinder 800 can be connected to an interface using clamping or securing device 806. As described, tube 138 can be configured to be attached at any angle 704. Further, gas cylinder 800 can supply a compressed gas through feed line 804. Gas flow can be adjusted using dial 808 and flow rate and/or gas tank pressure can be read on gauge 809. A common issue is that if a tube is disconnected from gas cylinder 800 while a hazardous gas is flowing into tube 138, gauge 809 will not change to a substantial degree to alert anyone of the disconnection. The presently described alarm devices, such as alarm device 100, are configured to produce an audible sound when tube 138 is disconnected from connection mechanism 128. This audible sound can be used to alert surrounding individuals that a disconnection has occurred and for the necessary person(s) to initiate a reconnection before a hazardous gas fills the surrounding area.

In some embodiments, gas cylinder 800 can be used to deliver oxygen to a patient and disconnection can be dangerous to the patient as described herein.

In some embodiments, alarm devices can be provided as kits. In one embodiment, an alarm device can be included in a kit with instructions for use.

In another embodiment, a kit can include an alarm device, instructions for use, and a nasal cannula.

In another embodiment, a kit can include an alarm device, instructions for use, and a gas delivery mask system.

Figure 9:
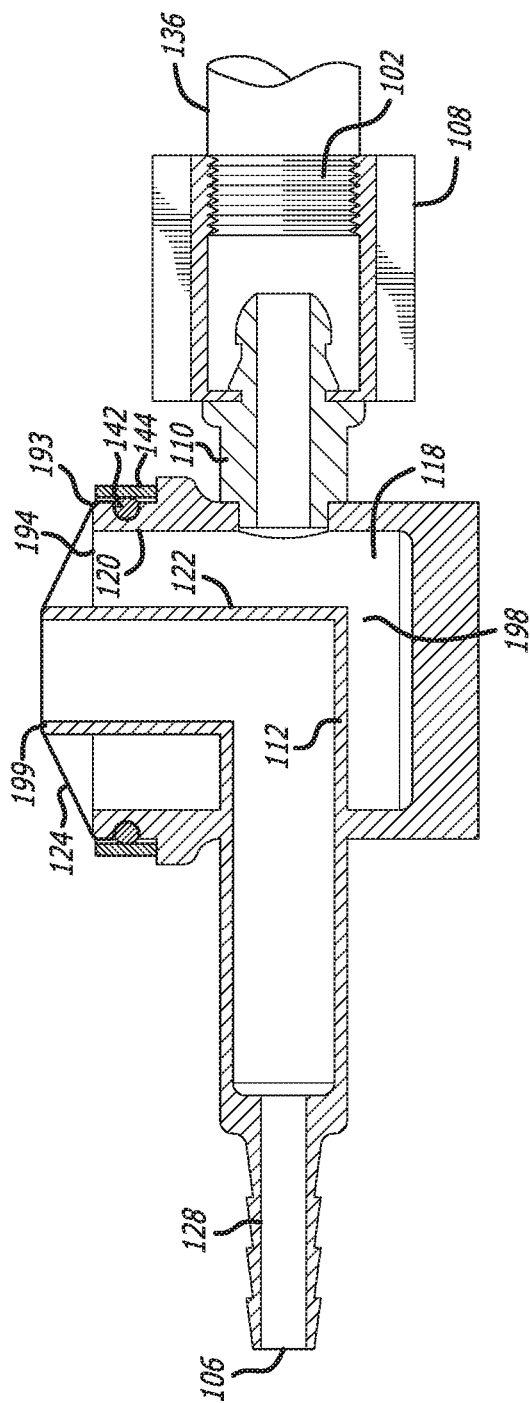
FIG. 9 is a side view of a non-limiting alarm device where the inlet and outlet are inline or axially aligned.

A non-limiting embodiment, alarm device 100 is illustrated in FIG. 9. As illustrated, gas inlet port 102, connection tube 110, and gas outlet port 106 can be inline or axially aligned. Internal pipe 112 can be configured to include an elbow 198 and extend from gas outlet port 106 to vibration member 124. Body end 194 can be fitted with vibration member 124 that attaches and seals to perimeter 193 of body end 194 thereby sealing internal volume 118. Vibration member 124 can extend over terminal end 199 of internal pipe 112 thereby sealing pipe interior from internal volume 118 until vibration member 124 is expanded or lifted at least partially off internal pipe 112. As described herein, vibration member 124 can create an audible sound when the gas delivery device is removed from the gas outlet.

Figure 10:
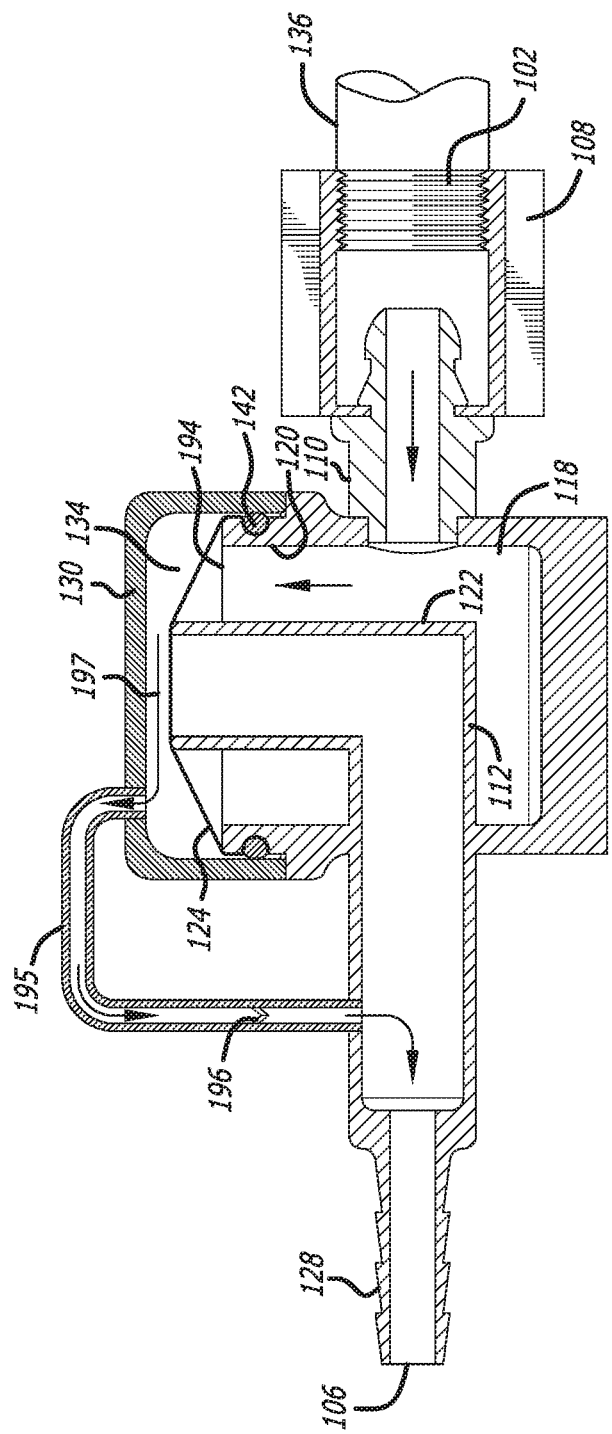
FIG. 10 is a side cross-sectional view of a non-limiting alarm device similar to that of FIG. 9 including a safety bypass.

Another non-limiting embodiment, alarm device 100, is illustrated in FIG. 10. As illustrated, gas inlet port 102, connection tube 110, and gas outlet port 106 can be inline or axially aligned. Cap 130 can be configured to cover vibration member 124 and the area around it. In some embodiments, cap 130 can protect vibration member 124 from physical damage that would otherwise occur from outside factors. In some embodiments, unlike FIG. 4, cap 130 can be configured without holes 132. Thus, space 134 between vibration member 124 and cap 130 can be at a given pressure and not allow outside air in.

In some embodiments, cap 130 can include a fail safe tube 195 that can allow flow between space 134 and internal pipe 112. Fail safe tube 195 can have a one way valve 196 to prevent airflow into fail safe tube 195 from internal pipe 112 during normal operation. During operation if vibration member 124 becomes punctured, sealed over body end 194, or otherwise becomes inoperable, fail safe tube 195 can prevent disruption of airflow to gas outlet port 106 by allowing airflow 197 through the fail safe tube and into internal pipe 112. Bypassing the inoperable vibration member 124 can prevent disruption of airflow during operation when replacing the device is not feasible.

In some embodiments, the herein described alarm devices can be used to confirm the existence of continuous gas flow. Confirming continuous gas flow can be of extreme importance in some instances. In such instances, the alarm can be left in the armed position to confirm the flow of gas by continuously alarming. This can be an audible confirmation of gas flow alerting to a correct situation instead of alerting to an undesirable situation, such as when a nasal cannula line becomes disconnected.

EXAMPLES

Example 1

A 35 year old male is prepared for surgery. An alarm device as described herein is attached to an operating room oxygen delivery system as described herein. A nasal cannula is connected to the alarm device and air flow is provided to the nasal cannula at about 2 L/min. The nasal cannula is placed at the patient's nose and the patient is placed under anesthesia for surgery.

During surgery, when the patient is under anesthesia and generally not aware of his surrounding, the nasal cannula tube becomes disconnected from the alarm device. As soon as the tube becomes disconnected, the alarm device produces a sound at a frequency of about 294 Hz. The sound appears to be that of a horn at about D above middle C or sharp of D.

The nearby nurse instantly understands that the sound is that of the alarm device indicating that the nasal cannula tube has become disconnected. She reconnects the tube to alarm device and the sound ceases and the patient's surgery resumes.

Example 2

An 78 year old female with severe dementia and pneumonia is admitted to the hospital. She is oxygen dependent because of her pneumonia. An alarm device as described herein is attached to a hospital oxygen delivery system in the form of an oxygen flowmeter as described herein. A nasal cannula is connected to the alarm device and oxygen flow is provided to the nasal cannula at about 4 L/min.

Overnight, the nasal cannula tube becomes disconnected from the alarm device as the patient shifts in her bed. As soon as the tube becomes disconnected, the alarm device produces a sound at a frequency of about 294 Hz. The nearby nurse instantly understands that the sound is that of the alarm device indicating that the nasal cannula tube has become disconnected. She reconnects the tube to alarm device and the sound ceases.

Without the alarm, it is possible that this severely demented patient would not be able to alert a health care provider for her need for oxygen. This situation is exacerbated in a scenario in which a patient is getting sedation for a procedure and is unconscious.

Example 3

A 64 year old female is unconscious but breathing at the scene of an automobile accident. Paramedics stabilize the woman. An alarm device as described herein is attached to an oxygen tank's outlet. A nasal cannula is connected to the alarm device and air flow is provided to the nasal cannula at about 2 L/min. The nasal cannula is placed at the woman's nose and the she is placed in the ambulance for transport to the hospital.

In route to the hospital, the nasal cannula tube becomes disconnected from alarm device as a result of a bump in the road during transport. As soon as the tube becomes disconnected, the alarm device produces a sound at a frequency of about 294 Hz. The sound appears to be that of a horn at about D above middle C or sharp of D. Despite the road noise, the alarm sound is loud enough for the attending EMT to hear. The EMT instantly understands that the sound is that of the alarm device indicating that the nasal cannula tube has become disconnected. He reconnects the tube to the alarm device and the sound ceases.

Example 4

A 65 year old male with emphysema with a baseline oxygen requirement is being discharged from the hospital after recovering from a pneumonia. An alarm device as described herein is attached to a hospital oxygen delivery system in the form of an oxygen flowmeter as described herein. A nasal cannula is connected to the alarm device and oxygen flow is provided to the nasal cannula at about 2 L/min.

As the patient is leaving, the hose for his nasal cannula is transferred from the wall oxygen flowmeter to his oxygen tank. As soon as the hose becomes disconnected, the alarm device produces a sound at a frequency of about 294 Hz. The sound appears to be that of a horn at about D above middle C or sharp of D. The nearby nurse instantly understands that the sound is that of the alarm device indicating that the oxygen has been left on even though the patient is now receiving oxygen from another source. She turns off the oxygen flow to the alarm device and the sound ceases thereby avoiding wasting oxygen. Since an open oxygen source is also a fire risk, fire risk is also reduced.

Example 5

A 35 year old male is prepared for surgery. An alarm device as described herein is attached to an operating room oxygen delivery system as described herein. A nasal cannula is connected to the alarm device and air flow is provided to the nasal cannula at about 2 L/min. The nasal cannula is placed at the patient's nose and the patient is placed under anesthesia for surgery.

After surgery, when the patient is transferred out of the operating room, the nasal cannula tube is disconnected from the alarm device. As soon as the tube becomes disconnected, the alarm device produces a sound at a frequency of about 294 Hz. The sound appears to be that of a horn at about D above middle C or sharp of D.

The nearby nurse instantly understands that the sound is that of the alarm device indicating that the oxygen has been left on even though the patient is now leaving the operating room. She turns off the oxygen flow to the alarm device and the sound ceases thereby avoiding wasting oxygen.

Example 6

A 35 year old male is to undergo surgery under sedation. An alarm device as described herein is attached to the anesthesia machine alternate oxygen flowmeter. A facemask is connected to the alarm device and oxygen flow is provided to the facemask at about 6 L/min. The facemask is placed over the patient's face for the duration of the surgery. During the surgery, the facemask tube is disconnected from the alarm device and immediately begins to produce a continuous sound at a frequency of between about 290 Hz and about 300 Hz. The sound appears to be that of a horn at about D above middle C or sharp of D. The operating room staff immediately knows there has been an interruption in the oxygen supply to the patient and the hose is reconnected.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An alarm comprising:
    an internal volume located between a gas inlet and a gas outlet,
    a non-powered vibration member, and
    a cap configured to at least partially cover the non-powered vibration member,
    wherein the non-powered vibration member is configured to produce an audible sound when a flow change occurs in the internal volume.

2. The alarm of claim 1, wherein the gas inlet is configured to attach to a gas source selected from a pressurized gas tank, an air pump, a rechargeable gas tank, a gas distribution system, or a combination thereof.

3. The alarm of claim 2, wherein the gas source is helium, nitrogen, argon, hydrogen, oxygen, carbon dioxide, halon, Freon, compressed air, propane, butane, carbon monoxide, hydrogen sulfide, ammonia, methane, nitrogen dioxide, acetylene, propylene, a hospital gas distribution system, or a combination thereof.

4. The alarm of claim 1, wherein the non-powered vibration member is located within a body portion, the body portion including an internal pipe extending beyond a proximal end of the body portion and connected to the gas outlet.

5. The alarm of claim 4, wherein the body portion is sealed against the internal pipe thereby creating an internal volume between an interior surface of the body portion and an exterior surface of the internal pipe.

6. The alarm of claim 5, wherein the non-powered vibration member is configured to attach to and seal the proximal end of the body portion thereby sealing the internal volume.

7. The alarm of claim 5, wherein the non-powered vibration member is configured to extend over a proximal end of the internal pipe thereby sealing the interior of the internal pipe from the internal volume.

8. The alarm of claim 5, wherein the non-powered vibration member is configured to expand or lift at least partially off a proximal end of the internal pipe thereby creating the audible sound.

9. The alarm of claim 1, wherein the audible sound is a musical note D, D above middle C, or sharp of D.

10. The alarm of claim 1, wherein the audible sound is produced by a flow rate less than about 15 L/min.

11. A kit including the alarm of claim 1 and instructions for use.

12. A kit of claim 11, further including a nasal cannula.

13. A kit of claim 11, further including a gas delivery mask.

14. A method of alerting that air flow is altered, the method comprising:
    attaching an alarm between a gas source and a gas outlet, wherein the alarm is configured to produce an audible sound when a pressure drop is detected,
    wherein the alarm includes a non-powered vibration member located between a gas inlet and the gas outlet.

15. The method of claim 14, wherein the non-powered vibration member is located within a body portion, the body portion including an internal pipe extending beyond a proximal end of the body portion and connected to the gas outlet.

16. The method of claim 15, wherein the body portion is sealed against the internal pipe thereby creating an internal volume between an interior surface of the body portion and an exterior surface of the internal pipe.

17. The method of claim 16, wherein the non-powered vibration member is configured to attach and seal to the proximal end of the body portion thereby sealing the internal volume.

18. The method of claim 16, wherein the non-powered vibration member is configured to extend over a proximal end of the internal pipe thereby sealing the interior of the internal pipe from the internal volume.

19. The method of claim 15, wherein the non-powered vibration member is configured to expand or lift at least partially off a proximal end of the internal pipe thereby creating the audible sound.

20. The method of claim 14, wherein the audible sound is a musical note D, D above middle C, or sharp of D.

* * * * *